US008829049B2

(12) United States Patent
Albuquerque et al.

(10) Patent No.: US 8,829,049 B2
(45) Date of Patent: Sep. 9, 2014

(54) MEDICINAL COMPOSITION INTENDED FOR THE TREATMENT OF ERECTILE DYSFUNCTION IN MAMMALS AND USE OF THE COMPOSITION

(75) Inventors: Sérgio Albuquerque, Ribeirão Preto-SP (BR); Jairo Kenupp Bastos, Ribeirão Preto-SP (BR); Paulo Sérgio Calefi, Brodowski-SP (BR); Katia Jorge Ciuffi, Ribeirão Preto-SP (BR); Wilson Roberto Cunha, Franca-SP (BR); Rosangela da Silva de Laurentiz, Ilha Solteira-SP (BR); Rodrigo Lucarini, Ilicinea MG (BR); Eduardo José Nassar, Ribeirão Preto-SP (BR); Ademar Alves da Silva Filho, Franca SP (BR); Márcio Luís Andrade e Silva, Franca SP (BR)

(73) Assignee: ACEF S.A., Franca (SP) (BR)

( * ) Notice: Subject to any disclaimer, the term of this patent is extended or adjusted under 35 U.S.C. 154(b) by 33 days.

(21) Appl. No.: 13/517,933

(22) PCT Filed: Dec. 21, 2009

(86) PCT No.: PCT/BR2009/000433
§ 371 (c)(1),
(2), (4) Date: Jan. 3, 2013

(87) PCT Pub. No.: WO2011/075801
PCT Pub. Date: Jun. 30, 2011

(65) Prior Publication Data
US 2013/0102660 A1    Apr. 25, 2013

(51) Int. Cl.
*A61K 31/36*    (2006.01)

(52) U.S. Cl.
CPC .................................... *A61K 31/36* (2013.01)
USPC .......................................................... 514/564

(58) Field of Classification Search
USPC .......................................................... 514/464
See application file for complete search history.

(56) References Cited

FOREIGN PATENT DOCUMENTS

| WO | 03080600 | 10/2003 |
| WO | 2006113981 | 11/2006 |
| WO | 2007009201 | 1/2007 |
| WO | 2009021347 | 2/2009 |

OTHER PUBLICATIONS

Vlachopoulos et al. (European urology 52 (2007) 1590-1600).*
Cicero et al., "*Lepidium meyenii* Walp. improves sexual behaviour in mal rates independently from its action on spontaneous locomotor activity," Journal of Ethnopharmacology (2005) 75:225-229.
MacKay, D., "Nutrients and Botanicals for Erectile Dysfunction: Examining the Evidence," Alternative Medicine Review (2004) 9(1):4-16.
Tharakan et al., "Botanical Therapies in Sexual Dysfunction," Phytotherapy Research (2005) 19:457-463.
Zhang et al., "Chemical Constituents of *Aristolochia constricta*: Antispasmodic Effects of Its Constituents in Guinea-Pig Ileum and Isolation of a Diterpeno-Lignan Hybrid," J. Nat. Prod. (2008) 71:1167-1172.

* cited by examiner

*Primary Examiner* — Shirley V Gembeh
(74) *Attorney, Agent, or Firm* — Volpe and Koenig, P.C.

(57) ABSTRACT

The use of cubebin, dibenzylbutyrolactolic lignan, its semi-synthetic and synthetic derivatives for the treatment of erectile dysfunction is shown and disclosed.

7 Claims, 4 Drawing Sheets

1a

1b

1c

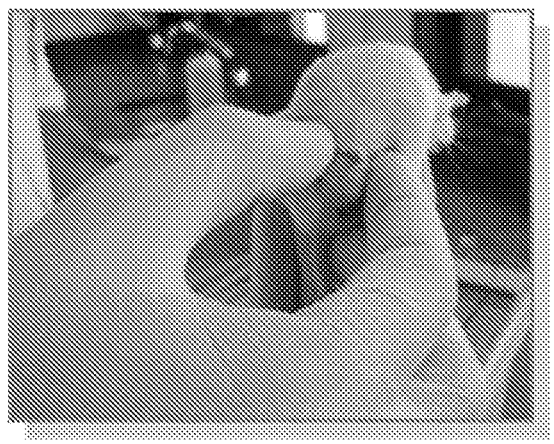
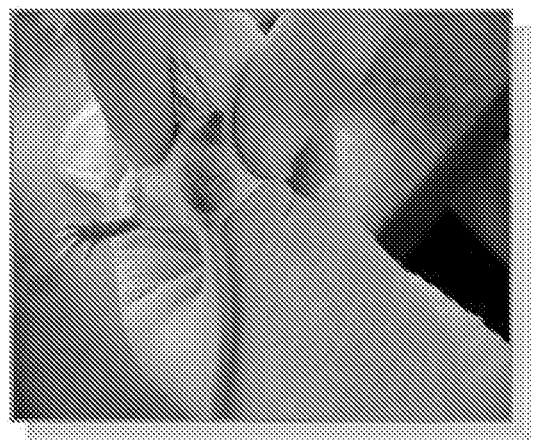
2a          2b
 
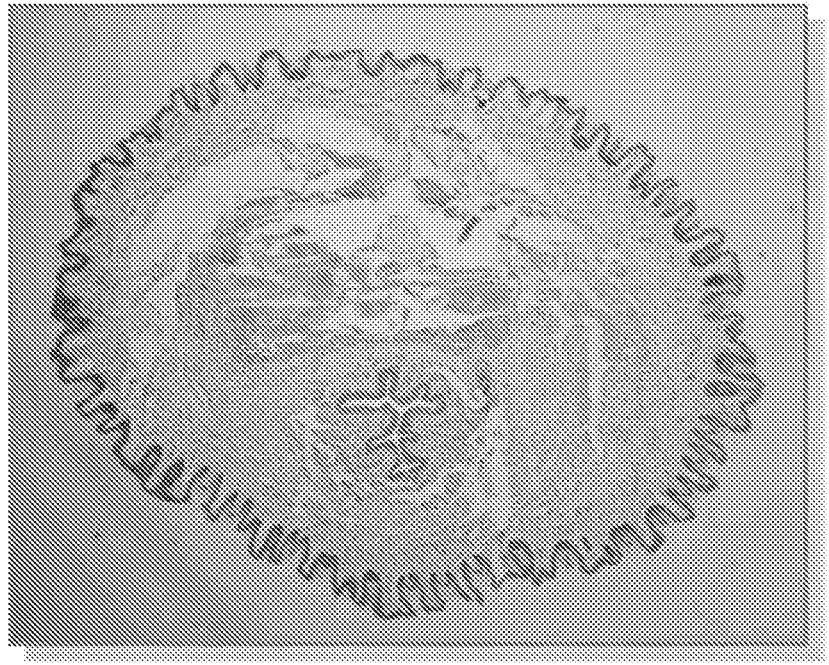
2c
Figures 2a, 2b, 2c

3a
3b
 
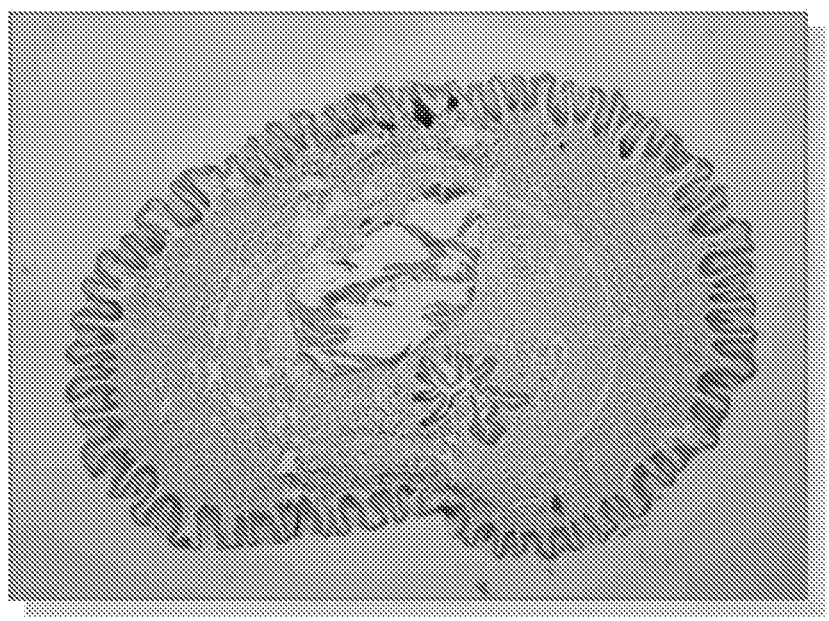
3c
Figures 3a, 3b, 3c 4a 4b 4c 4d

MEDICINAL COMPOSITION INTENDED FOR THE TREATMENT OF ERECTILE DYSFUNCTION IN MAMMALS AND USE OF THE COMPOSITION

This application is a 35 U.S.C. §371 national phase application of PCT/BR2009/000433, which was filed Dec. 21, 2009 and is incorporated herein by reference as if fully set forth.

The present invention refers to the use of lignans, such as dibenzylbutyrolactolic lignan, its semi-synthetic and synthetic derivates, especially cubebin, as vasodilator agents in the therapy of erectile dysfunction.

BASICS OF THE INVENTION

Erectile dysfunction (DE) is defined as the persistent inability to obtain and/or maintain appropriate penile rigidity to allow a satisfactory sexual intercourse, and it is responsible for a deep and significant compromise in the quality of life of men and their partners.

Prevalence data for DE in the literature varies according to the classification of the grade of the dysfunction. In Latin America, it is estimated that approximately 50% of 40 year-old or older men suffer some grade of DE and at least 3.5% have full dysfunction. Prospective studies indicate that about a million new DE cases appear each year in 40-70 year-old men in Brazil; in the United States (USA), only summing serious cases, there are 10 to 20 million men, but this number would increase to 30 million if we also considered DE in slight grade. In Brazil, it is estimated that there are about 25 million men with some grade of DE, of which 11 million have moderate or full DE.

DE cases are usually classified into four different kinds, according to their etiology: psychogenic, vasculogenic or organic, neurological and endocrine. It was believed for many years that psychological reasons were the main causes of said dysfunction. However, it is known today that DE caused by vascular problems is responsible for about 75% of the reported cases, while hypogonadism and psychological factors contribute with 19 and 14%, respectively.

Recent studies have shown that the prevalence of DE increases significantly with age. Certain grades of DE can be seen in 39% of more than 40-year old men and in 67% of more than 70-year old men (Feldman et al, 1994; Ganz, 2005). Although DE has both organic and psychogenic causes, it is known that said dysfunction is linked to atherosclerosis, dyslipidemias, hypertension, diabetes, sedentary life, smoking and obesity (Feldman et al, 2000). Behind premature ejaculation, this is the most common compromise of male sexual function.

Currently, DE is considered an important public health issue, due to its high prevalence, association to psychical suffering and important causes for male morbidity, due to its considerable prevalence. Projections for 2025 show about 322 million men with DE worldwide, and the highest prevalence rates should occur in developing countries, such as in Africa, Asia and South America.

The general anatomy of the penis is similar in all mammal species. Human penis consists of three cylindrical segments: a pair of corpora cavernosa located on the dorsal part and corpus spongiosum on the ventral part, surrounding the urethra and forming the penile gland on the distal portion. Each corpus cavernosum is surrounded by a fibrous and compact tissue, tunica albuginea, which is mostly constituted by collagen fibers, as well as some elastin fibers. The erectile tissue of corpora cavernosa is composed by multiple interconnected void spaces, covered by endothelial cells, besides trabeculae, forming the walls of the voids and consisting of thick bands of smooth muscle and a fibroelastic structure formed by fibroblasts, collagen and elastin. Corpora cavernosa are divided by a septum with holes, which is incomplete in human beings, allowing it to work as a single unit. Tunica albuginea of corpora cavernosa is 2-3 mm thick in flaccid state. Tunica albuginea of corpus spongiosum is less dense than corpora cavernosa and has more elastic fibers. The proximal part of the penis is anchored to the pelvic bone, and this region is called crura of corpora cavernosa, while the proximal part of corpus spongiosum forms the penile bulb. Both the crura and the bulb are connected to striated muscles. Penile bulb is surrounded by the bulbocavernosus muscle, while penile crura is surrounded by the ischiocavernosus muscle. The penile gland has the appearance of a sponge due to a vast venous plexus with a large number of anastomoses.

Erection is a complex physiological event comprising psychic, neural and vascular mechanisms, involving the interaction of neural stimulation of the smooth muscle of corpus cavernosum and the neuro-humoral release of contracting and relaxing factors from the endothelium. There are four main interconnected events occurring during erection: dilation of arteries and arterioles by the increase in blood flow in diastolic and systolic phases; storage of blood in peripheral sinusoid spaces, reducing venous efflux; straining of tunica albuginea for its capacity, occluding the emission veins and reducing venous efflux to its minimum.

During erection, the penis acts as a capacitor, accumulating blood under pressure since corpora cavernosa are relaxed. In flaccid state, arterioles and sinusoids are contracted, mainly by a adrenergic mechanisms, and exert maximum resistance to arterial inflow; in that state, only a small percentage of blood enters corpora cavernosa with nutritional purposes. At the same time sinusoids are contracted, veins freely drain to extrapenile veins. Thus, during this state, trabecular smooth muscles of corpora cavernosa and cavernosa and helicline arteries are kept in permanent contraction. Trabeculae are drained by emitting veins in communication with cavernosa veins and have oxygen pressure between 20 and 40 mmHg when the penis is in flaccid state. When the sympathetic activity is blocked, those muscles relax (tumescense), allowing arterial inflow and the consequent progressive increase of intracavernosum blood pressure. Only the blocked adrenergic activity, is not sufficient to reach a full penile erection state. The main events responsible for the state of erection are the relaxed cavernosum smooth muscles and heliclinal arteries, causing the maximum expansion of void spaces which end up by compressing under albugineous venous plexus.

During erection, smooth muscles of arterioles and sinusoids relax, consequently reducing peripheral resistance. Therefore, dilation of cavernosum and heliclinal arteries cause the increase in blood flow in the void spaces and the relaxed trabecular smooth muscle dilates the voids. Besides NO, NANC routes are responsible to release various other mediators causing the relaxation of the smooth muscle of the penis. Among them, we can mention neuropeptides, such as intestinal vasoactive peptide, peptide related to calcitonin gene, P substance, purines, such as adenosine triphosphate (ATP), decarboxylated amino acids, as well as paracrine agents such as prostaglandins, bradykinin and endothelial factors. Among anti-erectile modulators, we can mention, besides norepinefrin, neuropeptide Y and paracrine agents such as thromboxane, histamine, endothelin and angiotensin II.

The mechanism of penile erection has been calling attention for centuries. However, just in the last twenty years, physiology and molecular aspects of erection have been better elucidated. Cavernosum tissue of the penis can be compared to a sponge, composed by a net of communicating void spaces covered by vascular endothelium and separated by trabeculae, containing bundles of smooth muscle in a structure of collagen, elastin and fibroblasts. The fibroblast structure is, in fact, a continuation of tunica albuginea, fully involving the erectile tissue.

Recent applications of sophisticated clinical and scientific skills to the study of central (brain and spinal routes) and local (plain and endothelium muscle) mechanisms of penile erection have brought large progresses in the clinical management of erectile dysfunction. During the last decade, a large progress has been observed in DE treatment, extending from surgical methods (penile prosthesis or revascularization) until the recent development of efficient oral therapy. The efficacy of orally administered agents such as sildenafil, tadalafil, vardenafil represents the beginning of non-invasive pharmacological therapies in DE treatment.

The growing elucidation of physiological and biochemical bases for the erectile function in the last few years enabled to evolve the options for DE treatment. Penile prosthesis, the first used options for treatment which artificially supply rigid erection, are now reserved to the most serious cases of DE, and in other situations they are substituted with pharmacological agents planned to restore or activate biochemical mechanisms required for natural erection. Agents used for the treatment of erectile dysfunction have been classified according to their mechanism and place of action.

The use of an oral medicine for DE treatment is a relatively new method. Until slightly more than a decade, the availability of safe and efficient oral agents was practically unforeseeable. Nowadays, this therapy is largely available and new products are in final stages of evaluation before being sold. Firstly, oral pharmaceuticals were empirically used and their effectiveness was limited. Recently, after landmark discoveries in basic physiology and pharmacology, it has been possible to develop safe and useful compounds. While, until the early 1990s, testosterone could be considered as the only pharmaceutical with oral efficacy, various oral agents have been successfully used nowadays. Despite that, it is known that oral medication will never be effective in all cases where physiological mechanisms for penile erection are intact or moderately affected by local or systemic elements.

Introduced in therapeutics in 1988, the most widely used medicine in DE treatment is sildenafil citrate (Viagra®), as disclosed by the U.S. Pat. No. 6,469,012, a selective inhibitor for isoform 5 of phosphodiesterease enzyme (PDE 5) which can be classified as a conditioning agent for penile erection with peripheral action. With sexual stimulation, its action results in larger relaxing of penile muscles and consequently larger accumulation of blood in cavernosum sinusoid, causing a more rigid erection, with a recommended oral dosage between 50 and 100 mg approximately one hour before sexual intercourse. Sildenafil is quickly absorbed and maximum plasma concentrations are reached about sixty minutes after one single dose. Its half life in circulation is of four hours. The most common adverse effects are cephalea, red skin, dyspepsia, nose congestion and visual disturbances. These effects occur because PDE5 is not only present in corpus cavernosum, but also in other tissues such as the vascular bed and gastrointestinal tract. Since sildenafil increases GMPc levels, the subsequent product from stimulation of the NO-guanilate cyclase route, its use is not indicated for patients with DE using nitrates, since the vasodilator effect can be enhanced, causing serious hypotension. More than 500 deaths related to sildenafil have been reported, representing a rate of fifty deaths for each million prescriptions (MTKA, 2000).

Vardenafil is another PDE5 inhibitor as disclosed by the U.S. Pat. No. 6,362,178, commercially known as Levitra®, being ten times more powerful than sildenafil. Vardenafil is used in single doses of 10 or 20 mg, reaching maximum plasma concentration within 0.7 hours and 50% of patients have an erection thirty minutes after the ingestion. This pharmaceutical has similar pharmacokinetics and adverse effects to sildenafil. Safety tests show that vardenafil does not affect the ability of patients with coronary diseases and its combination with nitroglycerin shows minimum changes in heart rate and blood pressure.

Tadalafil (Cialis®) is another PDE5 selective inhibitor, as disclosed by the U.S. Pat. No. 7,182,958, recently introduced into the market. Its chemical structure is different from sildenafil and shows low activity against other PDEs. Clinical studies show that patients had erections twenty minutes after one single oral 20 mg dose and 60% still had effects 36 hours after the ingestion. Adverse effects are similar to sildenafil and vardenafil, but patients did not have red skin. Studies to evaluate the interaction between tadalafil and organic nitrates had modest synergic effects. However, just like sildenafil and vardenafil, taladafil should not be used with nitrates. It is now known that PDE5 inhibitors have reduced efficacy for DE treatment under conditions with lack of endogenous nitric oxide (NO), such as in diabetes, and thus PDE5 inhibitors releasing NO are being developed.

There are pharmaceutical forms for local (intracavernous, intraurethra and topic) application and for oral administration in the market. Oral administration is easy, non-invasive, easily reversible and tolerated both by the patient and by his partner. Therefore, orally administered pharmaceuticals have become the first choice therapy for a wide range of DE cases, among which sildenafil (Viagra) highlights. On the other hand, it is extremely important to develop pharmaceuticals with different mechanisms of action which may benefit patients not yet medicated by current therapies. Furthermore, different mechanisms of action can facilitate the simultaneous use of two pharmaceuticals, aiming for a synergic effect and better response in patients not responding to isolated therapies.

Any compound improving sexual activity has the potential to be extremely advantageous. Various natural products have been used for centuries as agents to improve male sexual function and are now under investigation. Unfortunately, there is no uniformly acceptable method to identify a substance improving the erectile function. However, experimental models in vivo have reported this hypothesis (McKay, 2004).

Current animal methods do not provide an accurate way to evaluate the erectile activity of a new compound. Animal models are only based on mechanical or instinctive sexual functions of observed animals. Furthermore, tests in humans can be of difficult interpretation due to the grade of subjectivity in self evaluation. Despite the complications, controlled and random studies are usually considered as the most precise method (McKay, 2004).

Many reasons have contributed to the introduction of plants in therapeutics, among which the fact that the population mistakenly believe that the natural origin makes the product less toxic than synthetic drugs. Furthermore, the pharmaceutical industry now understands that plants can be good business, since the population is also willing to use alternative ways of therapy.

Compounds derived from plants are traditionally used by different cultures with the object to improve sexual performance (Cicer et al, 2001). The search for natural products substantially contributes to the discovery of innovative pharmaceuticals or prototypes by the introduction of new chemical structures and/or mechanisms of action.

BRIEF DESCRIPTION OF THE DRAWINGS

The object of the present invention can be better understood from the detailed description as follows, which also reports the results of tests effected, which are shown by the following figures:

FIGS. 2a, 2b and 2c show the results of comparative tests in mice to which sildenafil citrate was administered;

FIGS. 3a, 3b and 3c show the results of negative control tests made with mice.

DETAILED DESCRIPTION OF THE INVENTION

Figure 1A:
FIGS. 1a, 1b and 1c show the results of tests in mice, to which cubebin was administered as per the present invention.

The use of lignans, especially cubebin, as a vasodilating agent in the therapy of erectile dysfunction has now been discovered and thus constitutes an object of the present invention. Particularly, cubebin is classified with CAS under the number 18423-69-3 and has the following formula:

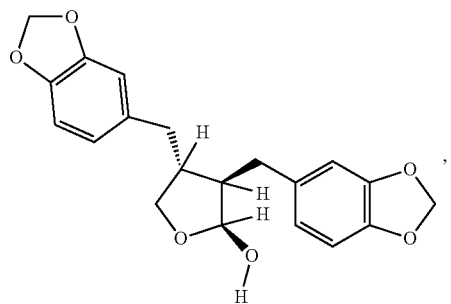 [SMILES: O[C@H]1OC[C@H](Cc2ccc3c(c2)OCO3)[C@H]1Cc1ccc2c(c1)OCO2]

as a vasodilating agent for the

Cubebin, as employed herein, is an active principle, which was initially but not exclusively extracted from seeds of *Piper cubeba*. Examples of processes to extract cubebin from another commercial source have been disclosed by the patent applications of the same inventor as follows: PI 0201237, filed on Mar. 25, 2002; PI 0501542, filed on Apr. 28, 2005; and PI 0503951, filed on Jul. 15, 2005. These references also disclose the processes to obtain/extract dibenzylbutyrolactolic lignan, its semi-synthetic and, synthetic derivatives.

To prove the efficacy of cubebin as a vasodilating agent in the therapy of erectile dysfunction, various laboratory tests have been effected with test animals, which are summarized below.

A. Animal Selection

42 Swiss mice have been used, adults, between 18 and 24 weeks old, weighing between 25 and 35 grams, from the Biotherium of the University of Franca (UNIFRAN), which were confined in plastic cages with metal fences and fed with standard feed (Labina-Purina) and water ad libitum, at room temperature of 22° C.

After a period of adaptation, the animals have been divided into seven groups, as per Table 1 below:

TABLE 1

| Group | Type | Administration |
|---|---|---|
| Group I: 6 mice | positive control | Each animal received 0.3 mg/kg of sildenafil citrate diluted in 0.5 saline solution (0.9%), intraperitoneally. |
| Group II: 6 mice | negative control | Each animal received 0.5 ml of saline solution (0.9%), intraperitoneally. |
| Group III: 6 mice | test group | Each animal received 20 mg/kg of cubebin diluted in 0.5 ml of saline solution (0.9%), intraperitoneally. |
| Group IV: 6 mice | test group | Each animal received 15 mg/kg of cubebin diluted in 0.5 ml of saline solution (0.9%), intraperitoneally. |
| Group V: 6 mice | test group | Each animal received 10 mg/kg of cubebin diluted in 0.5 ml of saline solution (0.9%), intraperitoneally. |
| Group VI: 6 mice | test group | Each animal received 5 mg/kg of cubebin diluted in 0.5 ml of saline solution (0.9%), intraperitoneally. |
| Group VII: 6 mice | test group | Each animal received 2.5 mg/kg of cubebin diluted in 0.5 ml of saline solution (0.9%), intraperitoneally. |

Animals from all groups have been kept under the same conditions for four hours for later evaluation of the studied pharmacological effect. They were subsequently anesthetized with a solution of 1.5 mg of ketamine plus 0.1 mg of xylazine and then euthanized to take off the penile tissue. Each sample was immediately stocked in 10% formaldehyde to make histological slides.

B. Results

The vasodilating effect has been observed within 35 to 45 minutes and remained active for 120 to 150 minutes for groups I and III.

Group I had tachycardia, shaking and testicle tumescence, while group III had prolonged erection and licked the penis.

Specifically, the statistical control of heart rate is summarized in the table below.

TABLE 2

| | Heart Rate Statistic Values | | | | | |
|---|---|---|---|---|---|---|
| | Negative control before | Negative control after | Positive control before | Positive control after | Cubebin before | Cubebin after |
| AVERAGE | 646.5 | 650.5 | 628.5 | 627.75 | 621.7 | 553.5 |
| DP | 27.5 | 110.1 | 67.3 | 131.7 | 59.3 | 125.1 |
| EPM | 13.5 | 55.1 | 33.9 | 65.8 | 29.6 | 62.6 |

Figure 1B:
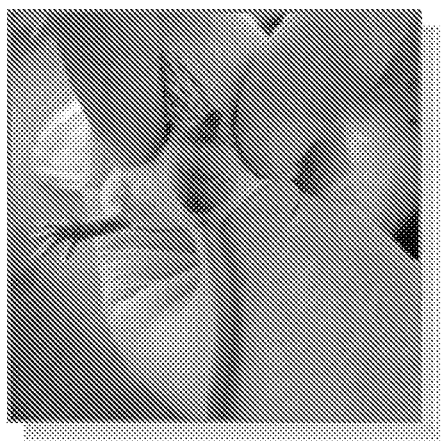
Figure 1C:
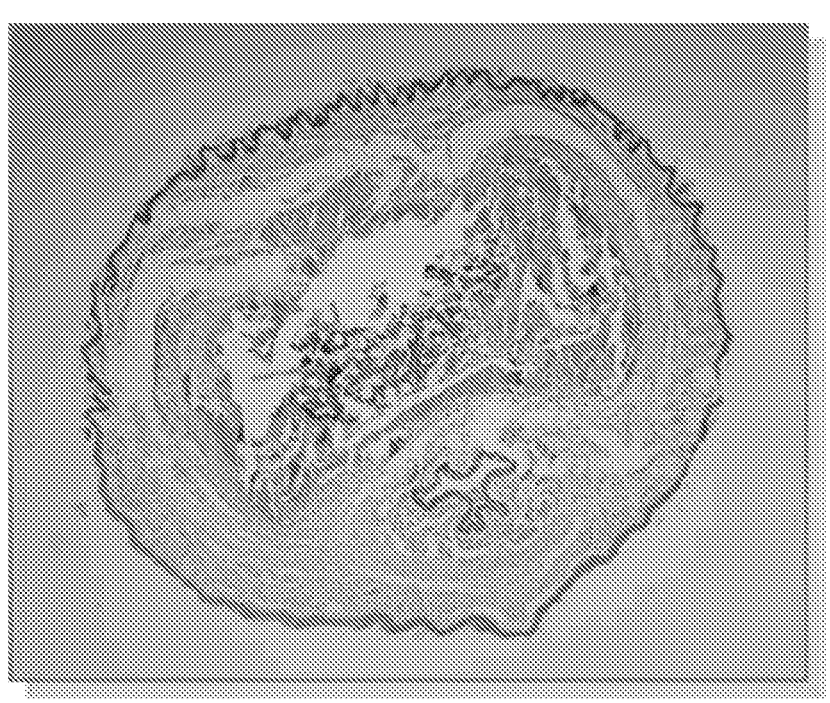
Figure 4A:
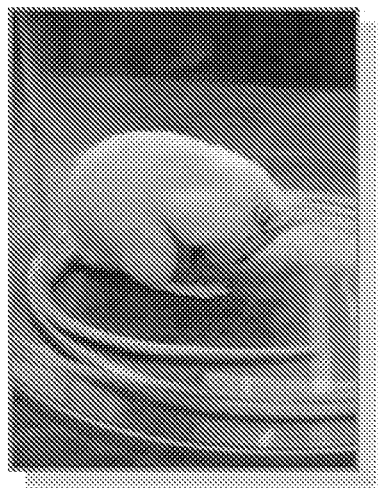
FIGS. 4a, 4b, 4c and 4d show the behaviour of mice after the administration of cubebin as per the present invention.
Figure 4B:
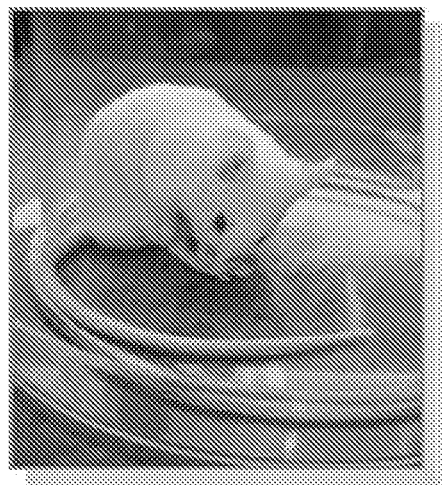
Figure 4C:
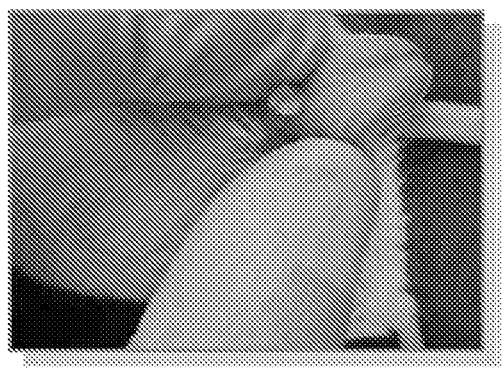
Figure 4D:

For better visualization of the results as obtained, FIGS. 1a and 1b show a microphotograph showing penile erection in the group treated with 20 mg of cubebin (Group III above), while FIG. 1c shows corpus cavernosum of a mouse of Group III treated with cubebin. FIG. 1c particularly shows the void space very dilated and congested (H. E., 400×). Furthermore, FIGS. 4a and 4b show a microphotograph showing the erection obtained from treatment with cubebin of elements from Group III above, while FIGS. 4c and 4d show microphotographs of the same animals ejaculating after said treatment, thus highlighting its vasodilating effect and sexual stimulation.

To compare the effects produced according to cubebin of the present invention, FIGS. 2a and 2b show a microphotograph showing penile erection in the group treated with 0.03 mg of sildenafil citrate (Viagra) (Group I) and FIG. 2c shows corpus cavernosum of a mouse treated that way. FIG. 2c shows the vascular space very dilated and full of erythrocytes (H. E., 400×).

A last comparison has been made from a negative control, wherein FIGS. 3a and 3b show a microphotograph showing that there was no penile erection in the negative control group and FIG. 3c shows the corpus cavernosum of a mouse included in said negative control group (Group II). FIG. 3c shows vascular voids visually contracted and with a lower volume of blood (HE, 400×).

Activity tests have been made for the enzyme phosphodiesterase 5 (PDE-5), which is responsible for vasodilation in gonads, culminating with penile erection. Results have confirmed the effect of cubebin and its derivatives for PDE-5. The 50% effective dose ($DE_{50}$) for cubebin was 16.6±8.20 µM and that of positive controls was 36.05±1.8 µM for sildenafil and 38.38±1.8 µM for hydroethylic desildenafil citrate.

From the above test results, we can see that the use of cubebin, as taught in the present invention, discloses positive results which are similar to the drugs as currently used for the treatment of male sexual impotence, particularly Viagra (sildenafil), administered to Group III, but not causing tachycardia or shaking.

What is claimed is:

1. A medicinal composition comprising cubebin for treatment of erectile dysfunction in a mammal, wherein the quantity of cubebin is between 2 mg and 8 mg per kg of the mammal.

2. The medicinal composition of claim 1, wherein the composition is administered by at least one route selected from the group consisting of intravenous, intramuscular, oral, rectal and parenteral.

3. The medicinal composition of claim 1, wherein the quantity of cubebin is 2 mg per kg of the mammal.

4. The medicinal composition of claim 1, wherein the quantity of cubebin is 8 mg per kg of the mammal.

5. The medicinal composition of claim 1, wherein the quantity of cubebin is between 2.5 mg and 5 mg per kg of the mammal.

6. A method of treating erectile dysfunction in a mammal comprising administering to the mammal a composition comprising cubebin in a quantity between 2 mg and 8 mg per kg of the mammal.

7. The method of claim 6, wherein the administering is by at least one route selected from the group consisting of intravenous, intramuscular, oral, rectal and parenteral.

* * * * *